US010456147B2

(12) United States Patent
Xiao

(10) Patent No.: US 10,456,147 B2
(45) Date of Patent: Oct. 29, 2019

(54) DEVICE FOR MINIMALLY INVASIVE BONE HARVESTING SURGERY

(71) Applicant: Zhejiang Furun Medical Technology Co., Ltd., Hangzhou (CN)

(72) Inventor: Jie Xiao, Hangzhou (CN)

(73) Assignee: Zhejiang Furun Medical Technology Co., Ltd., Hangzhou (CN)

(*) Notice: Subject to any disclaimer, the term of this patent is extended or adjusted under 35 U.S.C. 154(b) by 258 days.

(21) Appl. No.: 15/656,855

(22) Filed: Jul. 21, 2017

(65) Prior Publication Data

US 2018/0271543 A1 Sep. 27, 2018

(30) Foreign Application Priority Data

Mar. 21, 2017 (CN) .......................... 2017 1 0170645

(51) Int. Cl.
*A61B 17/16* (2006.01)
*A61B 17/00* (2006.01)
*A61B 90/00* (2016.01)

(52) U.S. Cl.
CPC .... *A61B 17/1635* (2013.01); *A61B 17/00234* (2013.01); *A61B 17/1617* (2013.01); *A61B 17/1626* (2013.01); *A61B 17/1633* (2013.01); *A61B 17/1628* (2013.01); *A61B 2017/00477* (2013.01); *A61B 2017/00969* (2013.01); *A61B 2090/032* (2016.02); *A61B 2090/034* (2016.02); *A61B 2090/035* (2016.02); *A61B 2090/036* (2016.02); *A61B 2090/064* (2016.02)

(58) Field of Classification Search
CPC .......... A61B 17/1635; A61B 17/00234; A61B 17/1617
See application file for complete search history.

(56) References Cited

U.S. PATENT DOCUMENTS

| 2,526,662 | A | * | 10/1950 | Hipps | ............... A61B 17/1635 408/67 |
|---|---|---|---|---|---|
| 6,071,284 | A | | 6/2000 | Fox | |
| 2010/0298835 | A1 | | 11/2010 | Ralph | |
| 2014/0018810 | A1 | | 1/2014 | Knape et al. | |
| 2014/0276840 | A1 | | 9/2014 | Richter et al. | |
| 2015/0025534 | A1 | * | 1/2015 | Gordon | ............. A61B 17/1635 606/80 |
| 2015/0202023 | A1 | | 7/2015 | Lee | |
| 2016/0270780 | A1 | | 9/2016 | Hall et al. | |
| 2017/0071610 | A1 | | 3/2017 | Lynch et al. | |

* cited by examiner

*Primary Examiner* — Christian A Sevilla
(74) *Attorney, Agent, or Firm* — Schwegman Lundberg & Woessner, P.A.

(57) ABSTRACT

A device for minimally invasive bone harvesting surgery described herein includes a cutter, a sleeve, and a drive control system. The cutter includes a head and a spiral conveying portion. An external screw thread is disposed on a surface of the spiral conveying portion, the sleeve is sleeved on the cutter, and the head and at least a part of the screw thread of the surface of the spiral conveying portion are exposed from the sleeve. The drive control system drives and controls the cutter to work. The device for minimally invasive bone harvesting surgery in this invention only needs a very tiny skin incision and bone window, cuts or grinds cancellous bone to bone fragments and then conveys them through a screw thread channel, which realizes the oriented conveying of the harvested bone.

15 Claims, 3 Drawing Sheets

DEVICE FOR MINIMALLY INVASIVE BONE HARVESTING SURGERY

CROSS-REFERENCE TO RELATED APPLICATIONS

This Non-provisional application claims priority under 35 U.S.C. § 119(a) on Patent Application No(s). 201710170645.3 filed in the People's Republic of China on Mar. 21, 2017, the entire contents of which are hereby incorporated by reference.

BACKGROUND OF THE INVENTION

Field of the Invention

This invention relates to a piece of medical equipment and, more particularly, relates to a minimally invasive electrical (or pneumatic) bone surgery device for cutting (grinding) bone tissue and orientedly conveying the cancellous bone particles which are cut off or grinded off.

Description of the Related Art

Bone grafting is a surgical procedure that transplants bone tissue to the bone defect part needing to be strengthened or fused inside a patient, commonly used in bone defects, nonunion of fractures, cavity filling after curettage due to bone diseases or bone tumors, or fusion of spine and joints, etc.

Clinical autogenous bone grafting has many advantages, such as good histocompatibility, no graft rejection reaction, and strong osteoinduction and so on, which has a good effect on promoting the bone fusion. The grafting part commonly used in the autogenous bone graft includes the part of ilium, tibia, upper fibula, rib, etc. Autogenous bone graft means taking down the sclerotin of the corresponding parts in the patient's own body and then transplanting to the bone defect site of the patient after processing. Take autogenous iliac bone graft for example. The prior art usually needs a incision of skin and soft tissue in a length up to several centimeters and a wider subperiosteal dissection, and then a widow is made on the ilium by an osteotome or the ilium is directly chiseled.

However, by these bone harvesting methods, in the process of cutting the ilium, more lateral femoral cutaneous nerve injury may occur, which leads to the numbness, pain, burning or acid sensation in the anterolateral area of the patient's leg. The bigger the cut bone is, the larger the corresponding incision is, and the higher the occurrence rate of the nerve injury is. In addition, pain in the bone harvest area, bone fracture of the bone harvest area, hematoma, infection, abdominal hernia, and ilioinguinal nerve injury also tends to occur in this case.

BRIEF SUMMARY OF THE INVENTION

To overcome the deficiencies of the prior art and solve the technical problem that the existing bone harvesting method has a large incision, is inconvenient to take the bone, and easily causes harm and leave sequelae to the patient, this invention provides a device for minimally invasive bone harvesting surgery, which only needs a very tiny skin incision and tiny bone window (of several millimeters in diameter), and bone fragments are cut (ground) from cancellous bone and then conveyed through a screw thread channel, which realizes oriented conveying of the cut or ground bone, easy operation, and quick surgery operation, thereby greatly reducing the harm to the patient caused during surgery, reducing the occurrence of the sequelea, and improving the safety of the surgery.

To achieve the above objective, the following technical solutions are adopted in this invention.

This invention provides a device for minimally invasive bone harvesting surgery, including a cutter, a sleeve, and a drive control system. The cutter includes a head and a spiral conveying portion; an external screw thread is disposed on a surface of the spiral conveying portion, the sleeve is sleeved on the cutter, the head and at least a part of the external screw thread of the surface of the spiral conveying portion are exposed from the sleeve; and the drive control system drives and controls the cutter to work by the combined effect of the head and the spiral conveying portion, achieving cutting or grinding bone tissue and oriented conveying at the same time.

The shape of the head in the invention may be a sphere, ellipsoid, umbrella, hemisphere, semi-ellipsoid, hemisphere+cylinder, semi-ellipsoid+cylinder, taper, or cylinder, and the head may be any of the head whose contact surface in contact with bone is a blunt contact surface.

Further, as an implementing mode of the invention, in an embodiment of the invention, a bone contact surface of the head in contact with bone tissue may be a blunt contact surface.

Further, as an implementing mode of the invention, in an embodiment of the invention, the head may be a blunt end which is not edged.

Further, as an implementing mode of the invention, in an embodiment of the invention, when the head is a blunt end which is not edged, a front end of the spiral conveying portion may be utilized to cut the bone tissue. At least one spiral blade which can cut the bone tissue may be disposed at the front end of the spiral conveying portion close to the head.

Further, as an implementing mode of the invention, in an embodiment of the invention, the surface of the not edged head may be smooth or matte.

Further, as an implementing mode of the invention, in an embodiment of the invention, the head may be provided with a cutting edge, and the center of an end of the head may be a blunt surface.

Further, as an implementing mode of the invention, in an embodiment of the invention, the head may be provided with a cutting edge, and the cutting edge may be a shallow cutting edge or a non-sharp cutting edge.

The spiral conveying portion has an external screw thread on its surface. In detail, for a more visual representation of the invention, the external screw thread structure may be refined into a plurality of spiral blades and spiral grooves. The spiral conveying portion may be provided with a plurality of spiral blades, and the spiral grooves may be formed between the spiral blades and a main body of the spiral conveying portion.

Further, the pitch of the spiral conveying portion may be 1-30 mm.

Further, the spiral angle of the spiral conveying portion may be 10°-89°.

Further, as an implementing mode of the invention, in an embodiment of the invention, the first spiral blade of the spiral conveying portion close to the head may be in connection with the head.

Further, as an implementing mode of the invention, in an embodiment of the invention, the first spiral blade of the spiral conveying portion close to the head may have a certain distance from the head, and the distance can ensure that the harvested bone tissue is smoothly conveyed backward along the spiral grooves of the spiral conveying portion.

Further, a major diameter of the first spiral blade of the spiral conveying portion close to the head may be less than that of other spiral blades. In other words, the screw thread of the front end of the spiral conveying portion may have a certain taper. Therefore, it can be ensured that during the cutting process of the bone harvesting device, the diameter of the screw thread of the front end in contact with the cortical bone may be relatively small, which makes the bone harvesting device can protect the cortical bone from being damaged by cutting during the bone harvesting process.

Further, as an implementing mode of the invention, in an embodiment of the invention, the diameter of the cross section of the sleeve may gradually increase from the position of the head along a direction away from the head. Certainly, in another embodiment of the invention, the sleeve may be a straight tube, that is, the diameter of the cross section of the sleeve is unchanged from the position of the head along the direction away from the head.

Further, as an implementing mode of the invention, in an embodiment of the invention, an edge of a front end surface of the sleeve may be rounded or chamfered.

The sleeve may be divided into two parts, which are the first part and the second part, wherein the first part may be close to the head, and the second part may be away from the head; the diameter of the cross section of the second part may be larger than that of the first part; and a depth limiting safety step may be disposed at the junction of the second part and the first part of the sleeve.

The diameter of the cross section of the sleeve may gradually increase from the position of the head along a direction away from the head; a front end surface of the sleeve may be provided with a chamfer or the front end surface may be provided as a slope, and an edge of the front end surface of the sleeve may retract backward, or a thickness of the edge may gradually increase backward.

Further, as an implementing mode of the invention, in an embodiment of the invention, the device for minimally invasive bone harvesting surgery may have a pressure limiting safety device.

Further, as an implementing mode of the invention, in an embodiment of the invention, the pressure limiting safety device may be a spring, and when the pressure of a front end of the head exceeds or is less than a set range, the spring may be compressed or released to control a motor to stop rotating.

Further, as an implementing mode of the invention, in an embodiment of the invention, the pressure limiting safety device may be a current detection device, the current of a motor may be detected, and when the current exceeds or is less than a set range, the motor may be controlled to stop rotating.

Further, as an implementing mode of the invention, in an embodiment of the invention, the pressure limiting safety device may be a pressure sensor, and when the pressure of the front end of the head is exceeds or is less than a set range, the motor may be controlled to stop rotating.

Compared with the prior art, the invention has the following advantages:

The basic work principle for the device for minimally invasive bone harvesting surgery: the cutter is driven by the motor to spin into the cancellous bone, such as the ilium, the end of the tibia and so on, cuts (grinds) the cancellous bone and then conveys the bone through the spiral conveying portion of the cutter, thereby achieving oriented and quick conveying of the solid content (bone particles).

The detailed operation process: at first, a minimally invasive incision is made in the skin of the surgical spot, such as the ilium, two ends of the tibia and so on, next an opening is made at the cortical bone of the surgical spot by a puncture hole opener (or a drill bit), and then the device for minimally invasive bone harvesting surgery in the invention is stretched into the opening. The device for minimally invasive bone harvesting surgery is turned on, the cutter driven by the electric (or pneumatic) motor cuts (or grinds) the bone tissue, and the cut granular or muddy bone is rapidly and orientedly conveyed through the spiral conveying portion connected behind the head. After operation, the device for minimally invasive bone harvesting surgery is turned off, and the head is pulled out. The cut granular or muddy bone conveyed orientedly can be collected in different methods for the autologous bone transplant of the patient. Using the sleeve and the head in a small diameter of the invention can cut (or grind) the cancellous bone under a minimally invasive incision, which leads to a tiny operation wound and a good operation result.

Using the present invention for operation, since the head of the device for minimally invasive bone harvesting surgery is tiny (the diameter of the head is several millimeters), it is easy to operate under the minimally invasive incision in the minimally invasive bone harvesting surgery. Only a small skin incision and bone window is needed to be cut for the patient, and the bone is cut (or ground) to be granular or muddy broken bone and then conveyed through the spiral conveying portion connected with the head rapidly and orientedly. Different collection methods can be used for the autologous bone transplant. The operation is quick, convenient, tiny-wounded, and of a good operation result. The tiny operation wound greatly reduces the risk of femoral lateral nerve injury, the pain of the surgical spot, the incidence of fracture and laparacele, and the infection rate of the surgical spot after operation. The device for minimally invasive bone harvesting surgery in the invention is easy operated and saves time and effort, and the valuable operation time is saved, which leads to a great convenience for the clinical operation.

These and other features, aspects, and advantages of the present invention will become better understood with regard to the following description, appended claims, and accompanying drawings.

DETAILED DESCRIPTION OF THE INVENTION

Embodiments

Figure 1:
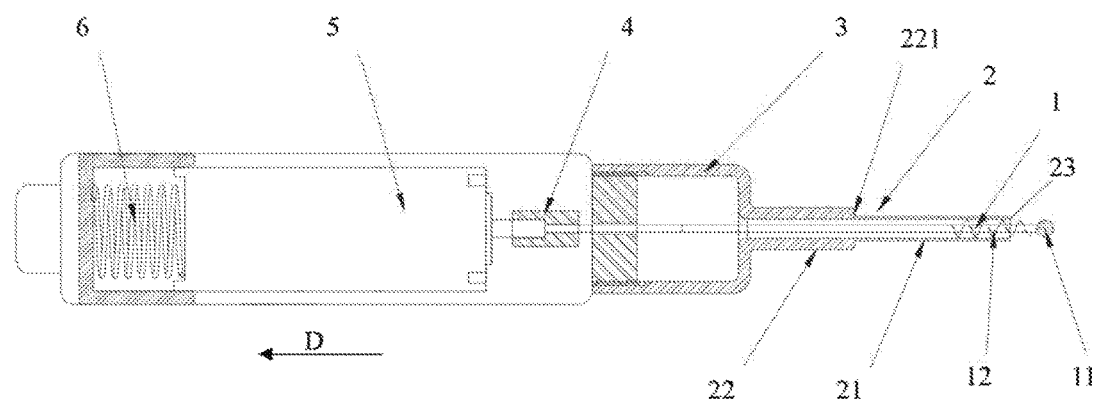
FIG. 1 is a structure schematic diagram of a device for minimally invasive bone harvesting surgery in an embodiment of the invention.

FIG. 1 is a structure schematic diagram of a device for minimally invasive bone harvesting surgery in an embodiment of the invention. As shown in FIG. 1, the device for minimally invasive bone harvesting surgery in this invention includes a cutter 1, a sleeve 2, a material collection device 3, and a drive control system 5.

Figure 2:
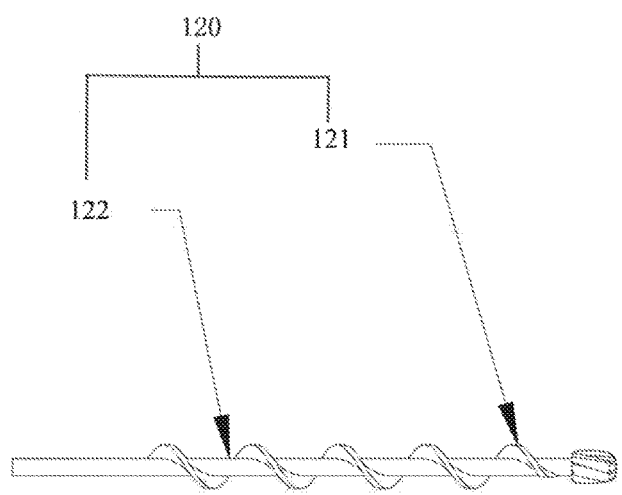
FIG. 2 is a structure schematic diagram of a cutter of the device for minimally invasive bone harvesting surgery in another embodiment of the invention.

FIG. 2 is a structure schematic diagram of a cutter in the device for minimally invasive bone harvesting surgery in another embodiment of the invention. As shown in FIG. 2, the cutter includes a head 11 and a spiral conveying portion 12.

The head 11 has a main effect of guiding the cutter deep into the bone tissue, the head 11 can be a grinding bit or drill bit, etc. The head 11 can be a blunt end in small diameter which is not edged and can also be provided with a plurality of cutting edges. In other words, in some embodiments, the head 11 may be a cutting head capable of cutting bone tissues; while in other embodiments, the head 11 may be a blunt head only capable of guiding the cutter into the bone tissue.

The shape and surface feature of the head 11 can be differently designed according to different demands. In this invention, to realize a better rotary cutting, the shape of the head is usually central symmetric. More particularly, the shape of the head may be a sphere, ellipsoid, umbrella, hemisphere, semi-ellipsoid, hemisphere+cylinder, semi-ellipsoid+cylinder, taper, or cylinder, and the head can be any of the head whose contact surface in contact with bone is a blunt contact surface.

If the head 11 is a blunt end in a small diameter which is not edged, the proper width of the widest position of the cross section of the blunt end is normally 1.2 mm-15 mm.

The surface of the head 11 can be a smooth surface or a matte surface.

The head 11 can also be provided with a cutting edge/blade. The cutting edge can be a central symmetric spiral cutting edge or a cutting edge with an irregularly disposed surface such as a chisel cutting edge, a longitudinal cutting edge, an oblique cutting edge and so on. The cutting edge of the head 11 can be straight, spiral, or inclined. To avoid hurting cortical bone, a shallow or non-sharp cutting edge is preferred when the cutting edge is disposed.

The spiral conveying portion 12 is disposed behind the head 11 and is co-axial with the head 11. FIG. 2 is the structure schematic diagram of the cutter in the device for minimally invasive bone harvesting surgery in an embodiment of the invention. As shown in FIG. 2, the spiral conveying portion 12 is provided with a plurality of spiral blades 121, and a plurality of spiral grooves 122 are formed. Cancellous bone harvested by the head 11 is conveyed backward along the spiral conveying portion 12. The length of the spiral of the spiral conveying portion 12 can be adjusted according to the actual needs.

When the head 11 is edged, the main work of the spiral conveying portion 12 is the transmission of the cut bone tissue. While the head 11 is a blunt end which is not edged, the cutting of the bone tissue is mainly relied on the spiral conveying portion 12, and at least one spiral blade 121 which can cut the bone tissue is disposed at the front end of the spiral conveying portion 12 close to the head.

The first spiral blade 121 of the spiral conveying portion 12 close to the head is connected with the head 11. Alternatively, a certain distance is provided between the first spiral blade 121 of the spiral conveying portion close to the head and the head, and the distance which is set properly can ensure that the harvested bone tissue is smoothly conveyed backward along the spiral grooves 122 of the spiral conveying portion 12.

In this embodiment, the thickness of the spiral blade 121 of the spiral conveying portion 12 is relative small, the width of each spiral grooves 122 is relative large, and the harvested bone tissue is conveyed by the spiral grooves 122.

In detail, the head 11 of the invention rotates and minces the cancellous bone, and the spiral conveying portion 12 conveys the cancellous bone backward. When the spiral conveying portion 12 rotates, due to the gravity of the materials and the friction force generated between the materials and the groove wall of the spiral groove 122 of the spiral conveying portion 12 and between the materials and the inner wall of the sleeve 2, the materials can only be moved backward along the groove bottom of the spiral groove 122 under the push of the spiral blade 121. The conveyance of the materials in the middle section mainly depends on the thrust force of the subsequently advanced materials. Thus, the conveyance of the materials along the conveying pathway of the spiral conveying portion 12 is a sliding movement. The rotating spiral blades 121 push to convey the materials, but the materials do not rotate with the spiral blades 121. The key is the gravity of the materials themselves, the friction force of the sleeve 2 against the materials and the reverse pressure generated when the cutter 1 is pushed forward and extrudes the cancellous bone.

An external screw thread 120 is disposed on the surface of the spiral conveying portion 12. FIG. 1 is the schematic diagram, where the external screw thread 120 is drawn only for illustration. In fact, the length of the spiral conveying portion 12 only needs to satisfy the smooth conveyance of the materials. In a preferred embodiment, in order to better complete the conveyance of the materials, the external screw thread 120 of the spiral conveying portion 12 is extended at least to the position of the material collection device 3.

Both of the above mentioned materials and the materials that may be mentioned hereinbelow refer to the cancellous bone harvested by the cutter of the device for minimally invasive bone harvesting surgery.

To realize the timely conveyance of the materials, as proved by a large number of experiments, the pitch of the spiral conveying portion can be 1 mm-30 mm, and the spiral angle thereof may be 10°-89°.

The sleeve 2 is sleeved on the cutter 1, and the head 11 and at least a part of the external screw thread 120 on the surface of the spiral conveying portion 12 are exposed out from the sleeve 2 during work. Generally speaking, at least a half circle of the screw thread 120 of the spiral conveying portion 12 is exposed out from the sleeve 2, and this is mainly for the cutting of the spiral blades 121 of the spiral conveying portion 12 if the head 11 has no cutting edge. Thus, at least a part of the screw thread 120 out of the sleeve 2 is needed. However, the exposed screw threads 120 or the spiral blades should not be too many, since the smooth backward conveyance of the harvested bone tissue also needs to be ensured.

The sleeve 2 is divided into two parts, which are the first part 21 and the second part 22, wherein the first part 21 is close to the head 11, and the second part 22 is away from the head 11. The diameter of the cross section of the second part 22 is larger than that of the first part 21. A depth limiting safety step 221 is disposed at the junction of the second part 22 and the first part 21 of the sleeve 2. The depth limiting safety step 221 can limit the depth of the cutter 1 entering the bone, thereby preventing the cutter 1 from penetrating the cortical bone. However, the invention is not limited thereto. In other embodiments, another protection mechanism or structure capable of effectively limiting the depth of the cutter 1 entering the bone may also be disposed at the junction of the second part 22 and the first part 21 of the sleeve 2.

The interior of the sleeve 2 is a hollow structure. The diameter of the cross section of the sleeve 2 gradually increases from the position of the head 11 along a direction D away from the head 11, and the increasing of the diameter of the cross section of the sleeve 2 from the front end to the back end (take the position of the head 11 as the front end) can ensure there is a large space for collecting the materials and can reduce the resistance of the conveyance of the materials, thereby conveying the materials more timely and effectively.

To further reduce the resistance, an edge 23 of a front end surface of the sleeve 2 can be rounded or chamfered. In other words, rounding or chamfering can be applied to the edge 23 of the front end surface of the sleeve 2. If the edge 23 is chamfered, the edge 23 can be chamfered inward or outward. In this way, the contact area between the device for minimally invasive bone harvesting surgery and the bone tissue can be reduced, thus to reduce the resistance incurred when the device is pushed forward. In other embodiments, a thickness of the side wall of the sleeve 2 can gradually increase backward, which can also reduce the resistance.

The material collection device 3 is connected with the sleeve 2, wherein a cavity is disposed. The cavity is communicated with the hollow body of the sleeve 2. The material conveyed by the spiral conveying portion 12 enters into the material collection device 3 for temporary storage, till the material collection device 3 is taken down to allow the bone tissue to be taken out after the bone tissue in a set value is harvested at one time.

The drive control system 5 drives and controls the cutter 1 to work, and the drive control system 5 mainly includes a motor and a control system. The invention also provides a coupling 4, which is used to connect the output shaft of the motor and the rotation shaft of the cutter 1, which make them rotate together to transmit the torque.

In addition, the device for minimally invasive bone harvesting surgery further has a pressure limiting safety device 6. In one embodiment of the invention, the pressure limiting safety device 6 is a spring, and when the pressure of the front end of the head exceeds or falls down a set range, the spring is compressed or released to control the motor to stop rotating. The pressure limiting safety device 6 can be located at the position as shown in the figures or can be located between the cutter and the motor or inside the cutter.

In another embodiment of the invention, the pressure limiting safety device 6 can be a pressure sensor, and when the pressure of the front end of the head 11 exceeds or is less than a set range, the motor is controlled to stop rotating, such that the advancement of the head 11 is prevented.

In another embodiment of the invention, the pressure limiting safety device 6 can be a current detection device, and when the current exceeds or is less than a set range, the motor is controlled to stop rotating, such that the advancement of the head 11 is prevented.

The pressure limiting safety device 6 can prevent the head 11 from further penetrating the cortical bone.

Embodiment 1

Figure 3:
FIG. 3 is a structure schematic diagram of the cutter of the device for minimally invasive bone harvesting surgery in Embodiment 1 of the invention.

FIG. 3 is a structure schematic diagram of the cutter in the device for minimally invasive bone harvesting surgery in Embodiment 1 of the invention. As shown in FIG. 3, the head in the embodiment is not edged, and the diameter of the head is small. The diameter of the head is the same as or slightly smaller than that of the body of the spiral conveying portion. The rotation direction of the spiral blades of the spiral conveying portion is opposite to that shown in FIG. 2. Since the head is not edged in this embodiment, the first spiral blade of the spiral conveying portion is utilized to realize the cutting of the bone tissue.

Embodiment 2

Figure 4:
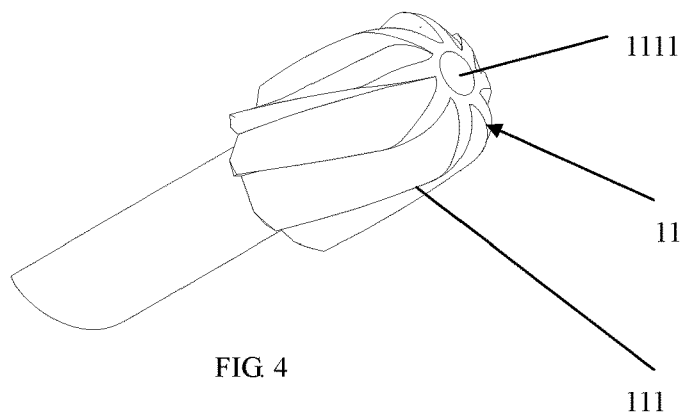
FIG. 4 is a structure schematic diagram of a head of the cutter of the device for minimally invasive bone harvesting surgery in Embodiment 2 of the invention.

FIG. 4 is a structure schematic diagram of the head of the cutter in Embodiment 2 of the invention. The head 11 has a plurality of spiral cutting edges 111, and none of the spiral cutting edges 111 reach the center 1111 of the end of the head 11. In other words, the center 1111 of the end of the head 11 is blunt, which is not edged. This is very important in this embodiment. The cutting edge of the head does not reach the center 1111 of the end of the head 11, which can ensure that the end of the head 11 has a blunt surface of a certain scale, such that the cutter is prevented from penetrating the cortical bone during the operation.

The front ends of the spiral cutting edges 111 of the head 11 are all acute angles. Aiming at the characteristics of autologous bone graft surgery, the head 11 of the invention is in a small diameter. The front ends of the cutting edges 111 are all acute angles, which can ensure that the end of the head 11 has a certain ability of piercing. However, since the hardness of the cortical bone is much greater than that of the cancellous bone, the cutter can pierce through the cancellous bone during the operation and avoid piercing through the cortical bone at the same time.

Embodiment 3

Figure 5:
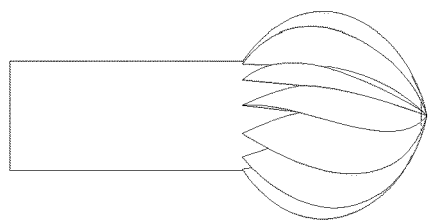
FIG. 5 is a structure schematic diagram of the head of the cutter of the device for minimally invasive bone harvesting surgery in Embodiment 3 of the invention.

FIG. 5 is a structure schematic diagram of the head of the cutter of the device for minimally invasive bone harvesting surgery in Embodiment 3 of the invention. As shown in FIG. 5, the head in this embodiment is spherical, and a plurality of spiral cutting edges are disposed on the head. The spiral cutting edges are oblique, and none of the spiral cutting edges reaches the center of the end surface of the head.

Embodiment 4

Figure 6:
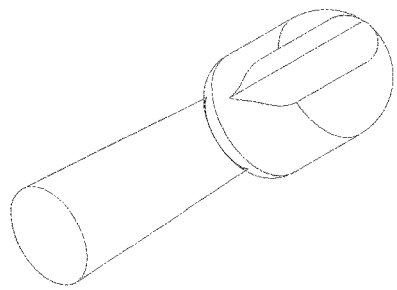
FIG. 6 is a structure schematic diagram of the head of the cutter of the device for minimally invasive bone harvesting surgery in Embodiment 4 of the invention.

FIG. 6 is a structure schematic diagram of the head of the cutter of the device for minimally invasive bone harvesting surgery in Embodiment 4 of the invention. As shown in FIG. 6, the head in this embodiment is approximately ellipsoidal, a single cutting edge is disposed at the head, and the cutting edge is disposed longitudinally. The front end and other surfaces of the head in contact with the bone tissues are all blunt surfaces.

Embodiment 5

Figure 7:
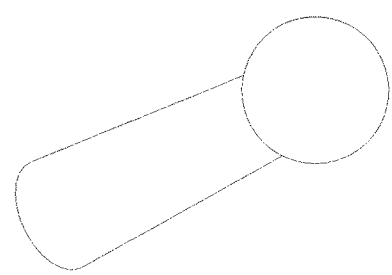
FIG. 7 is a structure schematic diagram of the head of the cutter of the device for minimally invasive bone harvesting surgery in Embodiment 5 of the invention.

FIG. 7 is a structure schematic diagram of the head of the cutter of the device for minimally invasive bone harvesting surgery in Embodiment 5 of the invention. As shown in FIG. 7, the head in this embodiment is spherical without cutting edges, and the surface can be a rough matte surface or a smooth surface. The diameter of the head is relatively slightly smaller than that of the edged head in the same type.

Embodiment 6

Figure 8:
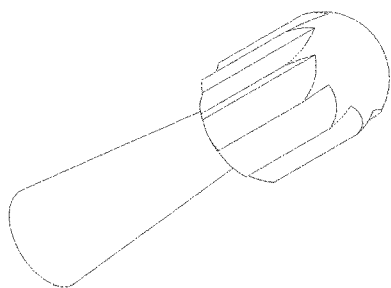
FIG. 8 is a structure schematic diagram of the head of the cutter of the device for minimally invasive bone harvesting surgery in Embodiment 6 of the invention.

FIG. 8 is a structure schematic diagram of the head of the cutter of the device for minimally invasive bone harvesting surgery in Embodiment 6 of the invention. As shown in FIG. 8, the head in this embodiment is approximately cylindrical, multiple cutting edges are disposed on the head, and the cutting edges are straight. None of the cutting edges reaches the center of the end surface of the head.

Embodiment 7

Figure 9:
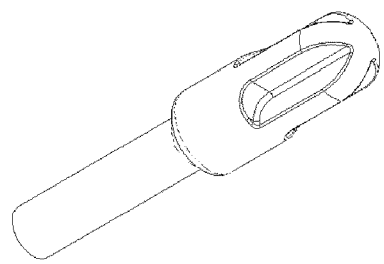
FIG. 9 is a structure schematic diagram of the head of the cutter of the device for minimally invasive bone harvesting surgery in Embodiment 7 of the invention.

FIG. 9 is a structure schematic diagram of the head of the device for minimally invasive bone harvesting surgery in Embodiment 7 of the invention. The shape of the head in the embodiment is a cylinder, multiple cutting edges are disposed on the head, and the cutting edges are non-sharp edges.

Embodiment 8

Figure 10:
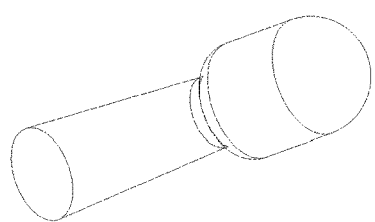
FIG. 10 is a structure schematic diagram of the head of the cutter of the device for minimally invasive bone harvesting surgery in Embodiment 8 of the invention.

FIG. 10 is a structure schematic diagram of the head of the cutter of the device for minimally invasive bone harvesting surgery in Embodiment 8 of the invention. The shape of the head in the embodiment is a cylinder which is not edged. The surface can be a rough matte surface or a smooth surface.

Embodiment 9

Figure 11:
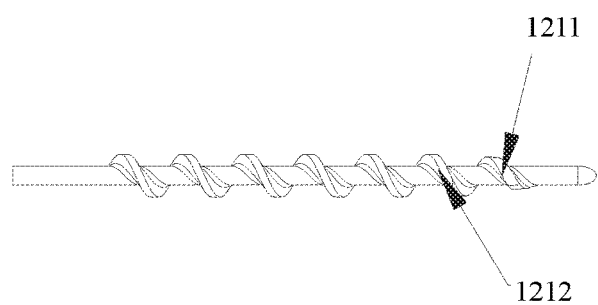
FIG. 11 is a structure schematic diagram of the cutter of the device for minimally invasive bone harvesting surgery in Embodiment 9 of the invention.

FIG. 11 is a structure schematic diagram of the cutter of the device for minimally invasive bone harvesting surgery in Embodiment 9. In this embodiment, a major diameter of the first spiral blade 1211 of the spiral conveying portion close to the head is less than that of other spiral blades 1212. In other words, the screw thread 120 of the front end of the spiral conveying portion has a certain taper. Therefore, it can be ensured that during the cutting process of the bone harvesting device, the screw thread 120 of the front end in contact with the cortical bone is relatively small, which makes the bone harvesting device be able to protect the cortical bone from being damaged by cutting during the bone harvesting process.

However, the invention is not limited thereto. In other embodiments, the cortical bone can be protected through other methods, and the screw thread 120 of the spiral conveying portion may not have the taper. In other words, the major diameter of the first spiral blade 1211 can be the same as that of other spiral blades 1212.

Although the invention is described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A device for minimally invasive bone harvesting surgery, comprising a cutter, a sleeve, and a drive control system, wherein the cutter comprises a head and a spiral conveying portion, an external screw thread is disposed on a surface of the spiral conveying portion, the sleeve is sleeved on the cutter, the head and at least a part of the external screw thread of the surface of the spiral conveying portion are exposed from the sleeve, and the drive control system drives and controls the cutter to work.

2. The device for minimally invasive bone harvesting surgery according to claim 1, wherein a bone contact surface of the head in contact with bone tissue is a blunt contact surface.

3. The device for minimally invasive bone harvesting surgery according to claim 1, wherein the head is a blunt end not edged.

4. The device for minimally invasive bone harvesting surgery according to claim 3, wherein a spiral blade capable of cutting bone tissue is disposed at a front end of the spiral conveying portion close to the head.

5. The device for minimally invasive bone harvesting surgery according to claim 1, wherein the head is provided with a cutting edge, and a center of an end of the head is a blunt surface.

6. The device for minimally invasive bone harvesting surgery according to claim 1, wherein the head is provided with a cutting edge, and the cutting edge is a shallow cutting edge or a non-sharp cutting edge.

7. The device for minimally invasive bone harvesting surgery according to claim 1, wherein the spiral conveying portion is provided with a plurality of spiral blades, spiral grooves are formed between the spiral blades and a main body of the spiral conveying portion, and a first spiral blade of the spiral conveying portion close to the head is connected with the head.

8. The device for minimally invasive bone harvesting surgery according to claim 1, wherein the spiral conveying portion is provided with a plurality of spiral blades, and spiral grooves are formed between the spiral blades and a main body of the spiral conveying portion, a certain distance is provided between a first spiral blade of the spiral conveying portion close to the head and the head, and the distance is capable of ensuring that harvested bone tissue is smoothly conveyed backward along the spiral grooves of the spiral conveying portion.

9. The device for minimally invasive bone harvesting surgery according to claim 1, wherein the spiral conveying portion is provided with a plurality of spiral blades, and a major diameter of a first spiral blade of the spiral conveying portion close to the head is less than that of other spiral blades.

10. The device for minimally invasive bone harvesting surgery according to claim 1, wherein the sleeve is hollow, the sleeve is divided into a first part and a second part, the first part is close to the head, and the second part is away from the head; a diameter of a cross section of the second part is larger than that of a cross section of the first part; and a depth limiting safety step is disposed at a junction of the second part and the first part of the sleeve.

11. The device for minimally invasive bone harvesting surgery according to claim 10, wherein a diameter of a cross section of the sleeve gradually increases from the position of the head along a direction away from the head.

12. The device for minimally invasive bone harvesting surgery according to claim 10, wherein an edge of a front end surface of the sleeve is rounded or chamfered.

13. The device for minimally invasive bone harvesting surgery according to claim 1, further comprising a pressure limiting safety device, wherein the pressure limiting safety device is a spring, and when the pressure of a front end of the head exceeds or falls below a set range, the spring is compressed or released to control a motor to stop rotating.

14. The device for minimally invasive bone harvesting surgery according to claim 1, further comprising a pressure limiting safety device, wherein the pressure limiting safety device is a current detection device, a current of a motor is detected, and when the current exceeds or falls below a set range, the motor is controlled to stop rotating.

15. The device for minimally invasive bone harvesting surgery according to claim 1, further comprising a pressure limiting safety device, wherein the pressure limiting safety device is a pressure sensor, and when a pressure of a front end of the head exceeds or falls below a set range, a motor is controlled to stop rotating.

* * * * *